US009267171B2

(12) United States Patent
Feng et al.

(10) Patent No.: US 9,267,171 B2
(45) Date of Patent: Feb. 23, 2016

(54) DNA PHOTOLITHOGRAPHY WITH CINNAMATE CROSSLINKERS

(71) Applicant: New York University, New York, NY (US)

(72) Inventors: Lang Feng, Jersey City, NJ (US); Paul Michael Chaikin, Pennington, NJ (US)

(73) Assignee: New York University, New York, NY (US)

( * ) Notice: Subject to any disclaimer, the term of this patent is extended or adjusted under 35 U.S.C. 154(b) by 24 days.

(21) Appl. No.: 14/194,327

(22) Filed: Feb. 28, 2014

(65) Prior Publication Data

US 2014/0256594 A1  Sep. 11, 2014

Related U.S. Application Data

(60) Provisional application No. 61/770,938, filed on Feb. 28, 2013.

(51) Int. Cl.
*C12Q 1/68* (2006.01)
(52) U.S. Cl.
CPC ............ *C12Q 1/6837* (2013.01); *C12Q 1/6876* (2013.01)
(58) Field of Classification Search
None
See application file for complete search history.

(56) References Cited

U.S. PATENT DOCUMENTS

| 5,013,830 | A | 5/1991 | Ohtsuka |
| 5,143,854 | A | 9/1992 | Pirrung et al. |
| 5,214,135 | A | 5/1993 | Srivastava |
| 5,264,423 | A | 11/1993 | Cohen et al. |
| 5,276,019 | A | 1/1994 | Cohen et al. |
| 5,434,049 | A | 7/1995 | Okano |
| 5,525,719 | A | 6/1996 | Srivastava et al. |
| 5,556,752 | A | 9/1996 | Lockhart et al. |
| 5,632,957 | A | 5/1997 | Heller et al. |
| 5,700,637 | A | 12/1997 | Southern |
| 5,744,305 | A | 4/1998 | Fodor et al. |
| 5,770,456 | A | 6/1998 | Holmes |
| 5,800,992 | A | 9/1998 | Fodor et al. |
| 5,807,522 | A | 9/1998 | Brown et al. |
| 5,830,645 | A | 11/1998 | Pinkel et al. |
| 5,830,653 | A | 11/1998 | Froehler et al. |
| 5,856,174 | A | 1/1999 | Lipshutz et al. |
| 5,959,098 | A | 9/1999 | Goldberg et al. |
| 5,965,452 | A | 10/1999 | Kovacs |
| 6,013,440 | A | 1/2000 | Lipshutz et al. |
| 6,022,963 | A | 2/2000 | McGall et al. |
| 6,045,996 | A | 4/2000 | Cronin et al. |
| 6,048,695 | A | 4/2000 | Bradley |
| 6,054,270 | A | 4/2000 | Southern |
| 6,063,338 | A | 5/2000 | Pham et al. |
| 6,258,606 | B1 | 7/2001 | Kovacs |
| 6,261,776 | B1 | 7/2001 | Pirrung et al. |
| 6,277,489 | B1 | 8/2001 | Abbott et al. |
| 6,277,628 | B1 | 8/2001 | Johann et al. |
| 2001/0008765 | A1 | 7/2001 | Shinoki |
| 2001/0012537 | A1 | 8/2001 | Anderson |
| 2001/0014448 | A1 | 8/2001 | Chappa |
| 2001/0014449 | A1 | 8/2001 | Nerenberg |
| 2001/0016322 | A1 | 8/2001 | Caren |
| 2001/0018642 | A1 | 8/2001 | Balaban |
| 2001/0019827 | A1 | 9/2001 | Dawson |

FOREIGN PATENT DOCUMENTS

| WO | WO 92/03568 | 3/1992 |
| WO | WO 96/17958 | 6/1996 |
| WO | WO 97/46313 | 12/1997 |
| WO | WO 98/13526 | 4/1998 |
| WO | WO 99/09217 | 2/1999 |
| WO | WO 99/51773 | 10/1999 |

OTHER PUBLICATIONS

Yoshimura et al. (2005) "Interstrand photocrosslinking of DNA via p-carbamoylvinyl phenol nucleoside" Bioorganic & Medicinal Chemistry Letters 15(5):1299-1301.*
Stec et al., Automated Solid-Phase Synthesis, Separation, and Steroechemistry of Phosporothioate Analogues of Oligodeoxyribonucleotides, *J. Am. Chem. Soc.* vol. 106, No. 20, pp. 6077-6079, 1984.
Stec et al., "Solid-Phase Synthesis, Separation, and Sterochemical Aspects of P-Chiral Methane- and 4,4'-Dimethoxytriphenylmethaneophosphonate Analogues of Oligodeoxyribonucleotides", *J. Org. Chem.*, vol. 50, No. 20, pp. 3908-3913, 1985.
Stec et al., Reversed-Phase High-Performance Liquid Chromatographic Separation of Diastereomeric Phosphorothioate Analogues of Oligodeoxyribonucleotides and Other Backbone-Modified Congeners of DNA, Journal of Chromatography, 1985. 326:263.
LaPlanche et al., Phosphorothioate-modified oligodeoxyribonucleotides. 111. NMR and UV spectroscoptc studies of the Rp-Rp, Sp-Sp, and Rp-Sp duplexes, [dCGGsAATTCC)],, derived from diastereomeric 0-ethyl pbospborothfoates, , 1986. Nuc. Acid. Res. 1986. 14:9081.
Lamond., 2'-0=Akl yloligorib onucleotides: Probes for Studying the Biochemistry and Cell Biology of RNA Processing, 1993. *Biochem. Soc. Trans.* 21:1.
Uhlmann et al., "Antisense Oligonucleotides: A New Therapeutic Principle", Chemical Reviews, vol. 90, No. 4, Jun. 1990, pp. 543-584.
Sonveaux, E., "Protecting Groups in Oligonucleotide Synthesis", Methods in Molecular Biology, vol. 26, Protocols for Oligonucleotide Conjugates, 1994, pp. 1-71.

(Continued)

*Primary Examiner* — Tracy Vivlemore
*Assistant Examiner* — Karen S Weiler
(74) *Attorney, Agent, or Firm* — Foley & Lardner LLP

(57) ABSTRACT

The present invention relates generally to cinnamate crosslinkers. Specifically, the present invention relates to gels, biochips, and functionalized surfaces useful as probes, in assays, in gels, and for drug delivery, and methods of making the same using a newly-discovered crosslinking configuration.

8 Claims, 9 Drawing Sheets

(56) References Cited

OTHER PUBLICATIONS

Agrawal. *Methods in Molecular Biology* 26:1, Protocols for Oligonucleotide Conjugates, Humana Press, 1994, Table of Contents.
McNeal, et al., A New Method for Sequencing Fully Protected Oligonucleotides Using 252Cf-Plasma Desorption Mass Spectrometry. *J. Am. Chem. Soc.*, 1982, 104, 976-980.
Viari, et al., Sequence Analysis of Unprotected Tri-Deoxyribonucleoside Diphosphates by 252 Cf-Plasma Desportion Mass Spectrometry, *Biomed. Environ. Mass Spectrom.* vol. 14, pp. 83-90 (1987).
Grotjahn et al., "Ultrafast sequencing of oligodeoxyribonucleotides by FAB-mass spectrometry", *Nuc. Acid Res.* vol. 10, No. 15 (1982), p. 4671-4670.
Bergot et al., "Separation of synthetic phosphorothioate oligodeoxynucleotides from their oxygenated (Phosphodiester) defect species by strong-anion-exchange high-performance liquid chromatography", Journal of Chromatography 599 (1992) pp. 35-42.
Sambrook et al., Molecular Cloning: a Laboratory Manual, Second Edition (1989), 27 pages, Table of Contents.
DNA Cloning, vols. I and II (DN Glover Ed. 1985), 11 pages, Table of Contents.
(Gait, M.J. IRL Press at Oxford University Press. 1984), Oligonucleotide Synthesis, A Practical Approach; Table of Contents.
A Practical Guide to Molecular Cloning (1984); or the series, Methods in Enzymology (Academic Press, Inc.)), Table of Contents.

Johnston, "Gene chips: Array of hope for understanding gene regulation", Curr. Biol. vol. 8, No. 5, pp. R171-R174, 1998.
Schummer, "Inexpensive Handheld Device for the Construction of High-Density Nucleic Acid Arrays", Biotechniques 23:1087-1092, 1997.
Smith, "Direct Hybridization of Large-Insert Genomic Clones on High-Density Gridded cDNA Filter Arrays", Biotechniques 23:120-124, Jul. 1997.
Solinas-Toldo, "Matrix-Based Comparative Genomic Hybridization: Biochips to Screen for Genomic Imbalances", Genes, Chromosomes & Cancer 20:399-407, 1997.
Bowtell, "Options available—from start to finish—for obtaining expression data by microarray", Nature Genetics Supp. vol. 21, pp. 25-32, Jan. 1999.
Bischoff et al., "Introduction of 5'-Terminal Functional Groups into Synthetic Oligonucleotides for Selective Immobilization", Anal. Biochem. 164:336-344, (1987).
Kremsky et al., "Immobilization of DNA via oligonucleotides containing an aldehyde or carboxylic acid group at the 5' terminus", Nucl. Acids Res. vol. 15, No. 7:2891-2910, (1987).
Chu et al., "Low fluorescence background electroblotting membrane for DNA sequencing", Electrophoresis 13:105-114, 1992.
Hames, B.D., et al, "Nucleic Acid Hybridisation, a Practical Approach", IRL Press, Oxford, Washington, D.C., 6 pages (1984), Table of Contents.

\* cited by examiner a
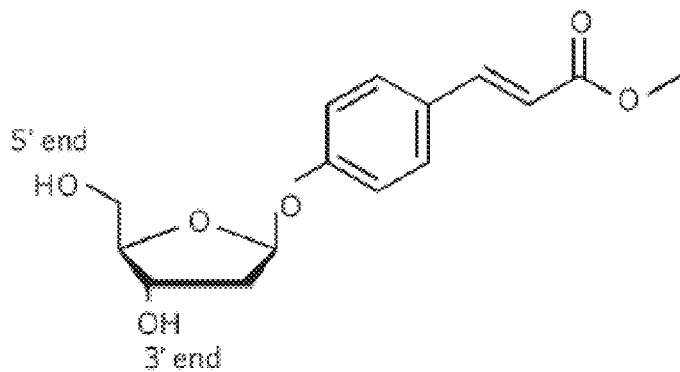
b Head-to-head cycloaddition:
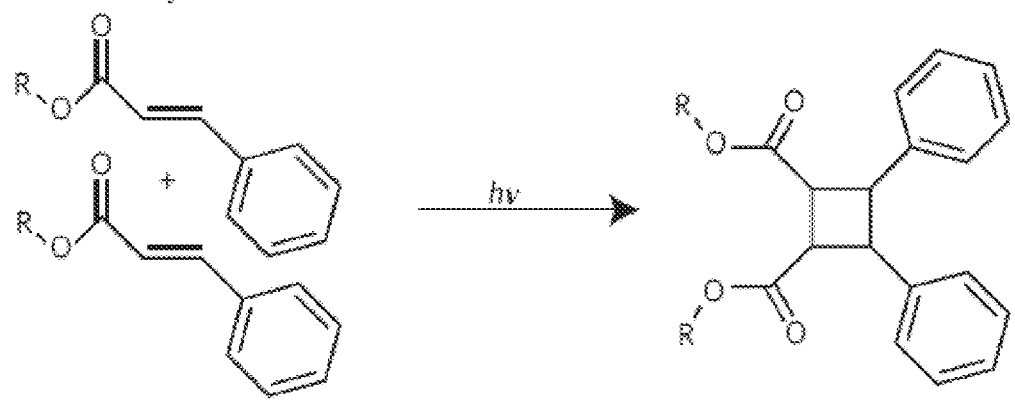
Head-to-tail cycloaddition:
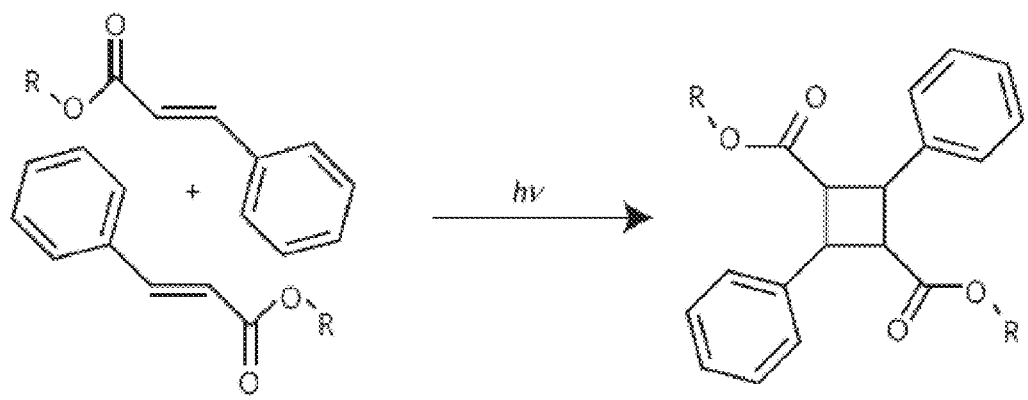
Figures 1A-B

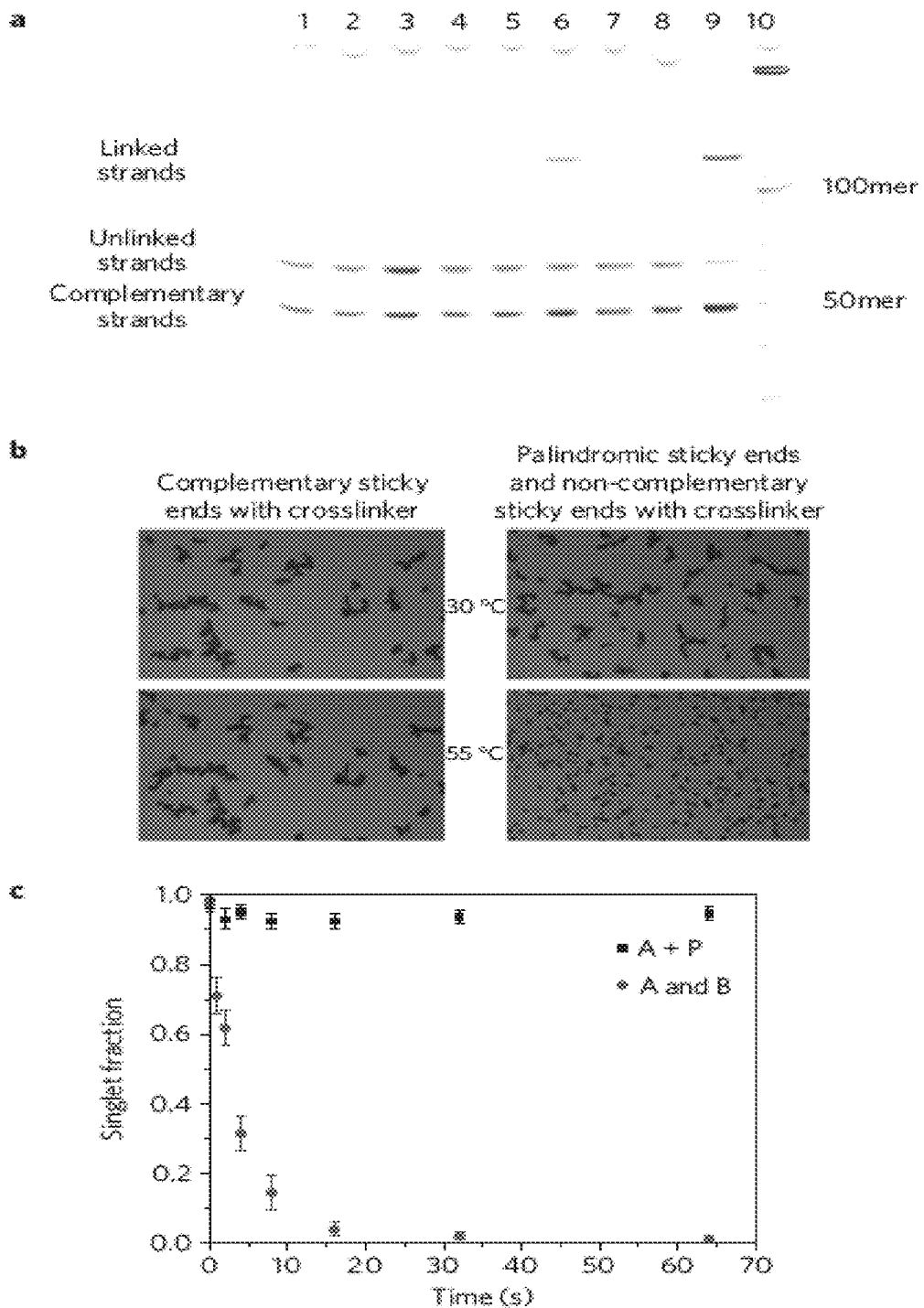
Figures 2A-C

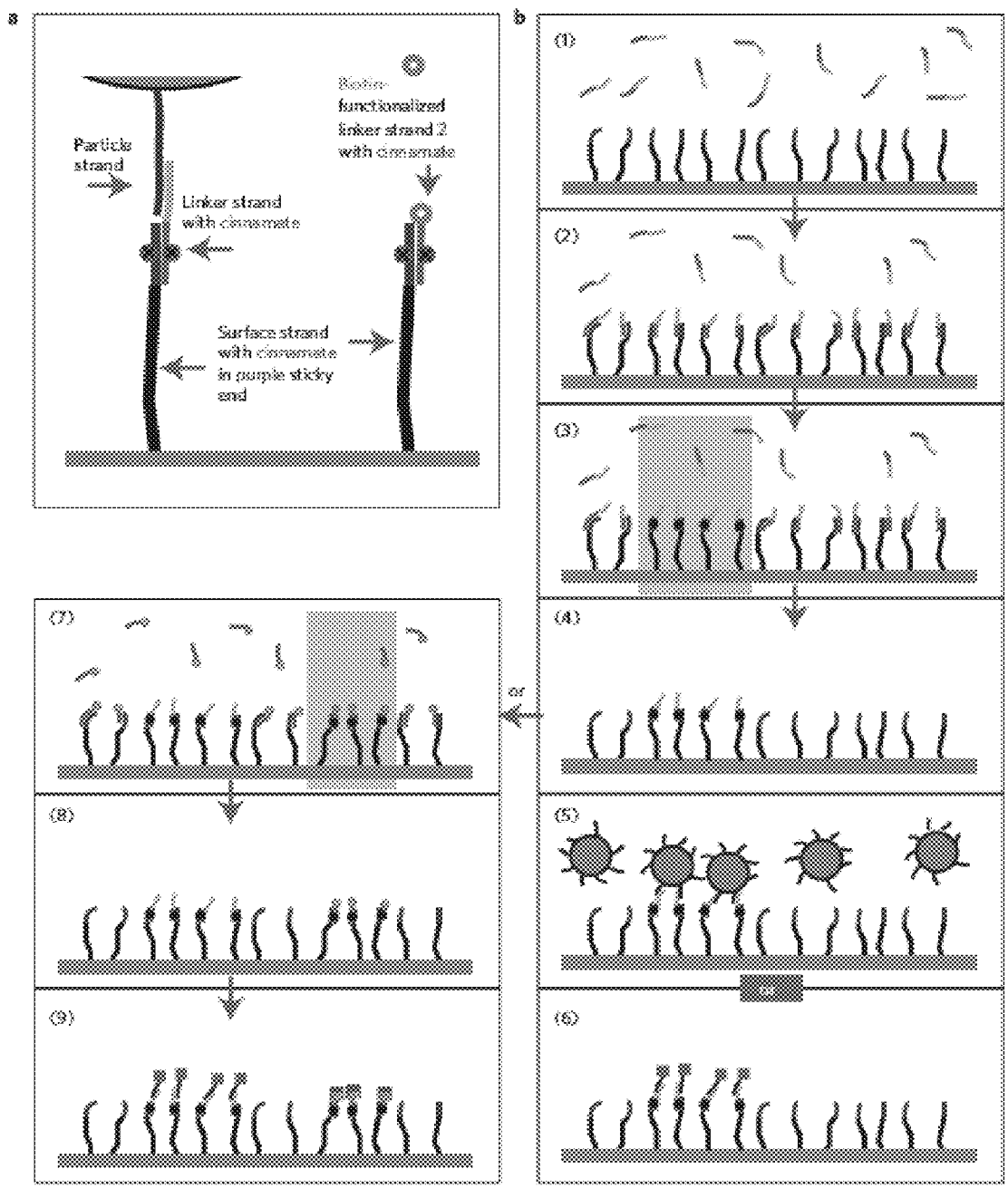
Figures 3A-B

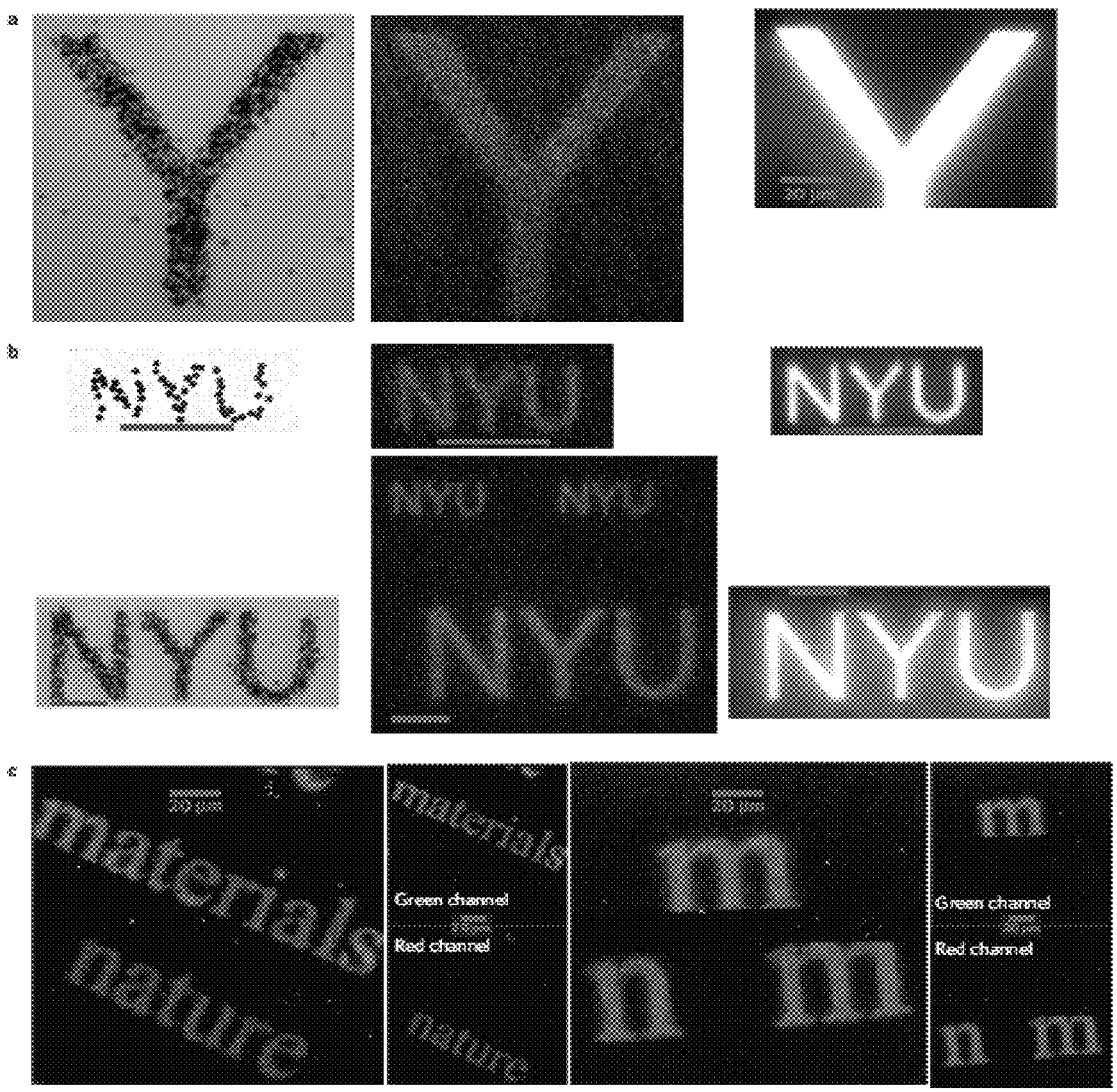
Figures 4A-C

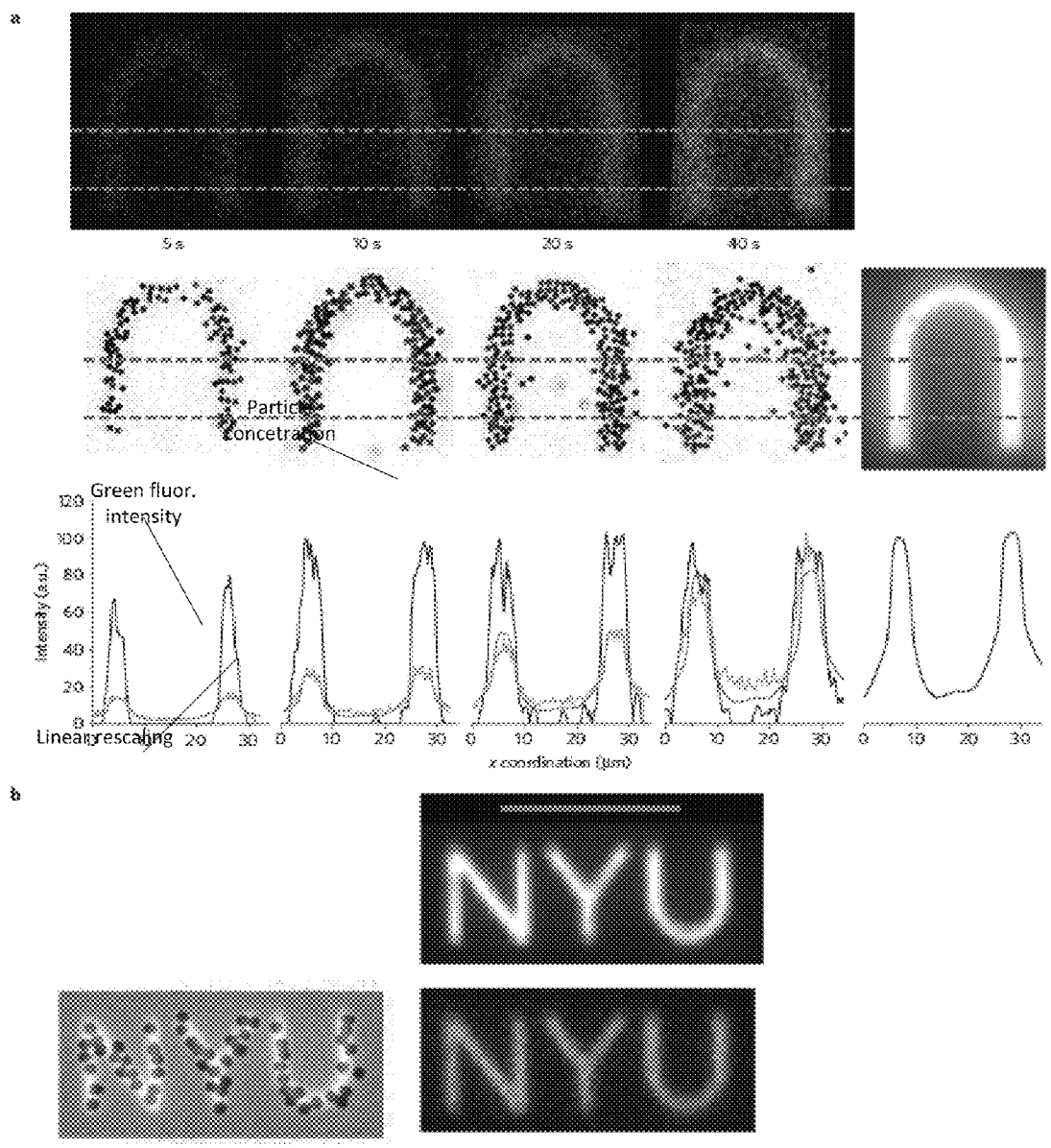
Figures 5A-B

Figures 7A-B

DNA PHOTOLITHOGRAPHY WITH CINNAMATE CROSSLINKERS

CROSS REFERENCE TO RELATED APPLICATIONS

This application claims priority to U.S. Provisional Application No. 61/770,938 filed Feb. 28, 2013, herein incorporated by reference in its entirety.

STATEMENT OF GOVERNMENT-SPONSORED RESEARCH

This invention was made with United States government support awarded by the following agencies: MRSEC Program of the National Science Foundation (Award No. DMR-0820341), NASA (Award No. NNX08AK04G), the National Institute of General Medical Sciences (GM-29554), the National Science Foundation (CTS-0608889 and CCF-0726378), the Army Research Office (48681-EL and W911NF-07-1-0439), and the Office of Naval Research (N000140910181 and N000140911118). The United States government may have certain rights in the invention.

SEQUENCE LISTING

The instant application contains a Sequence Listing which has been submitted electronically in ASCII format and is hereby incorporated by reference in its entirety. Said ASCII copy, created on May 16, 2014, is named 046434-0442_SL.txt and is 4,361 bytes in size.

FIELD OF THE INVENTION

The present invention relates generally to DNA hybridization techniques for use in creation of functional DNA surfaces. Specifically, the present invention relates to the use of cinnamate as a cross-linker in DNA-directed nano-particle structures.

BACKGROUND OF THE INVENTION

Complex self-assembly processes require components to associate with particular partners in a preprogrammed fashion. DNA functionalization of nanoconstructs, nanoparticles, and micron-scale colloids has proven effective in getting specific cohesion between pairs of components and in forming structures. The hybridization behavior of DNA has been extensively studied for decades. Aside from genetic detection, DNA hybridization has been used to build designable DNA nano-structures, DNA-directed nano-particle structures, and micron particle structures. Such DNA engineering techniques can be utilized for DNA computing (processors), and in DNA chips, multifunctional colloidal particles as used in drug delivery, and complex colloidal self-assembly.

The highly specific, thermoreversible paired interactions that are formed by complementary DNA strands play an important role in biology and have recently been exploited as key building blocks particularly in nanotechnology as a strategy to selectively bind and create a host of potentially important structures and functional systems including crystals, motors/robots, computers, replicators, and machines. It is highly desirable to crosslink some or all of these bonds permanently for nanotechnological applications, as well as for biological assays. Several crosslinking methods have been investigated previously. Psoralen, a highly exploited crosslinking agent, intercalates between hybridized thymidine-adenosine dinucleosides in a DNA sequence and reacts with the thymines upon exposure to UV light, forming covalent links. However, the crosslinking efficiency for psoralen in solution is low (effective cross section $5 \times 10^{-6}$ nm$^2$) or requires a very specific attachment of the psoralen group at the start of a DNA "sticky end" next to a T-A sequence.

Cinnamate is one of the most extensively studied photocrosslinkers used in DNA hybridization. Cinnamate-functionalized polymers are known to undergo crosslinking via photocycloaddition reactions upon exposure to UV radiation. Generally, cinnamate attaches to DNA strands using a phosphoramidite group, wherein a cinnamate on one strand is photo-crosslinked with an adjunct adenine base on another strand. However, the crosslinking efficiency is low, requiring approximately 30 minutes of incubation time for hybridization given an intensity of about 5.7 mW/cm$^2$.

There remains, therefore, a need for efficient, specific, and permanent DNA crosslinking methods for use in biological assays, drug delivery, processors, and other nanoparticle structures.

SUMMARY OF THE INVENTION

The present invention is based on the discovery that cinnamate groups may be substituted for a base pair and covalently bonded on complementary hybridized nucleic acid strands, developed to address the problems with existing techniques outlined above.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

In one aspect, the present invention provides a composition, such as an aggregate or a liquid dispersion, comprising a first substrate having at a first surface nucleic acid strand comprising a first cinnamate functional group or derivative thereof and forming a first sticky end, a second substrate having a second surface nucleic acid strand comprising a second cinnamate functional group or derivative thereof and forming a second sticky end, the first sticky end and the second stick end substantially complementary and hybridizable with each other; wherein the first colloidal particle and the second colloidal particle are covalently bonded via the first cinnamate group and the second cinnamate functional group.

In some embodiments, the covalent bonding is the result of a hybridization step and a subsequent UV exposure step. Such a hybridization step may take place as a result of a heating step. In further embodiments, the 5' end of the nucleic acid strand may be connected to a tetraethylene glycol spacer terminated by a biotin group. The sticky end may, in some embodiments, have a sequence of 5'-TACG-linker-CGTA-3', and the linker may be cinnamate or a derivative thereof. The UV exposure step may, in still further embodiments, take place for less than 30 minutes, less than 20 minutes, less than 15 minutes, less than 10 minutes, less than 5 minutes, less than 15 seconds, or less than 10 seconds at an intensity of 3.6 mW/cm$^2$.

In another aspect, a biochip is provided a support substrate a functional nucleic acid surface strand bound to the support substrate; the surface strand hybridized from its 5' end with a complementary nucleic acid strand, the 3' end of each surface nucleic acid strand having a sticky end comprising cinnamate or a derivative thereof; and at least one linker strand comprising a surface strand portion complementary to the sticky end of the surface strand and comprising cinnamate covalently bound with the cinnamate of the surface strand the linker and a target portion comprising a sticky end having a sequence substantially complementary to a target material.

In some embodiments, the substrate may be substrate selected from the group consisting of a membrane, glass, plastic, or a bead. In further embodiments, the surface may be multifunctional. In still further embodiments, the surface strand may be bound to the surface via a thiol, via biotin-streptavidin chemistry, or via amine chemistry such as amidine-NHS interaction. The covalent bonding may, in some embodiments, be achieved via the steps of (1) annealing the linker strand to the surface strand by decreasing the temperature from about 50° C. to about 25° C., and (2) permanently cross-linking the strands by application of UV, optionally further comprising the steps of reheating the biochip to about 50° C. and washing the biochip with eluent to remove the hybridized linker strand.

Another aspect of the present invention provides a method of photolithography comprising exposing a functionalized surface to conditions such that a linker strand hybridizes to a surface nucleic acid strand, exposing desired portions of the functionalized surface to UV light for less than 30 minutes, removing excess linker strand, and treating the functionalized surface with a target analyte, particle, or sequence; wherein each surface nucleic acid strand is hybridized from its 5' end with a complementary nucleic acid strand having fewer unpaired nucleotides than the surface nucleic acid strand such that one base acts as a hinge and at least two unpaired bases are left as a sticky end, the sticky end further comprising a cinnamate linker; and wherein the linker strand comprises two parts, a portion complementary to the sticky end of the surface nucleic acid and comprising a cinnamate, and a second portion complementary to a sticky end of an target analyte, particle, or sequence.

In some embodiments, the hybridization conditions comprise a decrease in temperature from about 50° C. to about 25° C. In further embodiments, the step of removing excess linker strand comprises increasing the temperature of the surface to about 50° C. and/or washing the surface with an eluent solution. The target may, in some embodiments, be a probe, nucleic acid-tagged particle, or a biologically active agent. Furthermore, the desired portions for patterning may be between about 1 μm and about 500 μm, between about 1 and about 200 μm, or between about 1 and about 50 μm.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 1A-B are a schematic representation of cinnamate-containing nucleoside and cycloaddition products. FIG. 1(A) demonstrates the cycloaddition between two cinnamate groups, with only E isomers shown, and their potential configurations, and FIG. 1(B) shows the cinnamate-containing nucleoside for incorporation into DNA;

FIG. 2(A) shows the results of a 10% denaturing electrophoretic gel on samples with and without crosslinking; FIG. 2(B) is a set of micrographs of the aggregation of DNA-coated 1 micron colloidal particles; and FIG. 2(C) is a histogram showing the fraction of unaggregated particles as a function of UV exposure time for particles with and without crosslinkers;

FIG. 3(A) is a schematic showing DNA constructs and the position of cinnamate crosslinkers. FIG. 3(B) is a schematic showing a procedure to make a multi-functional DNA surface, with steps (1)-(2) showing hybridization of a linker strand to a surface strand from 55 to 25° C. in half an hour; step (3) showing a permanent UV cross-link between the surface and linker strands in areas with a black dot; step (4) showing a de-hybridization of unlinked strands at 55° C.; step (5) showing reversibly binding colloids to the patterned regions, and step (6) showing the use of fluorescently labeled complementary DNA strands;

FIGS. 4A-B illustrate DNA photolithographic patterns: Right: exposed patterns with different feature sizes (←14 μm in a and 4 and 1.5 μm in b); left:colloid patterns (inverted so unstuck particles have escaped); middle: green fluorescently labelled conjugate images. FIG. 4C is illustrates multi-functionalized patterns of 'nature materials' (abbreviated as 'n m') in New Times Roman font. Left: green fluorescently labelled DNA hybridizes to the LS patterned in the region 'materials,' and red streptavidin binds to the LS2-patterned biotin in the region 'nature'. Right: similar patterning of larger 'n' and 'm' letters. Separate confocal filtering channels are shown as smaller figures. All scale bars are 20 μm;

FIG. 5(A) is a set of fluorescent images (first row) and colloid images (second row) and the exposed pattern, and a graph of the intensity profile between the dashed lines along the x axis FIG. 5(B) is a set of photographs superimposing the colloidal images and fluorescent images with the exposed pattern (scale bar at 20 μm);

DETAILED DESCRIPTION OF THE PREFERRED EMBODIMENTS

Figure 6:
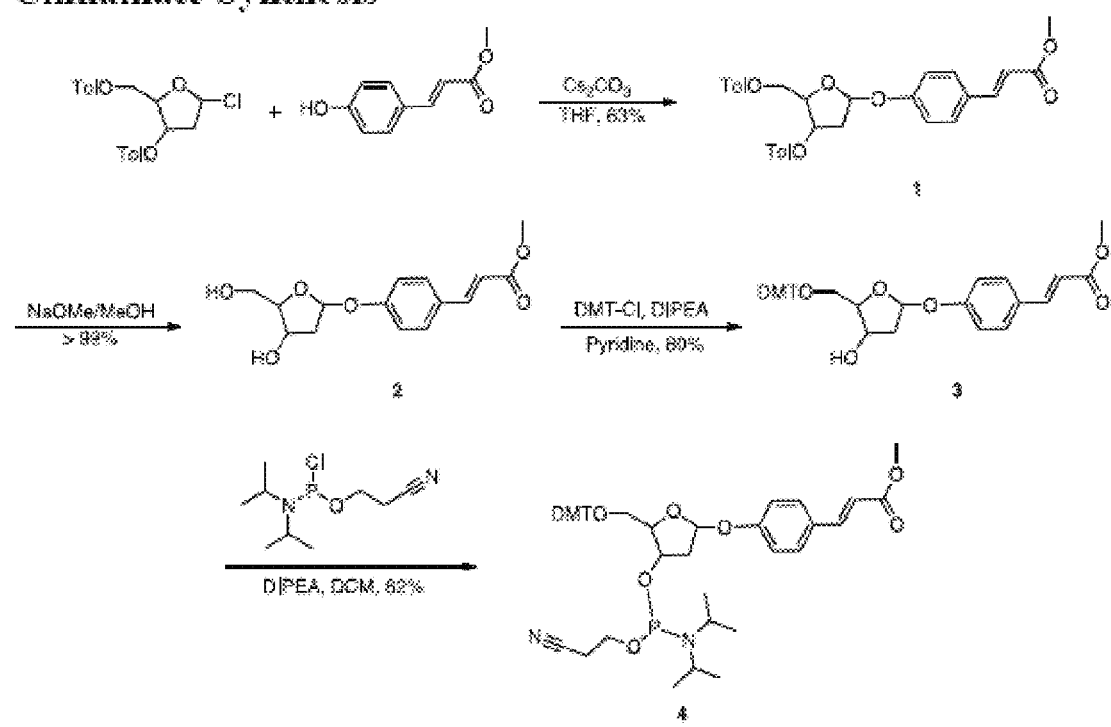
FIG. 6 is a schematic showing a common route for the synthesis of cinnamate.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

The present invention is based upon the discovery that cinnamate groups may be substituted for a base pair and covalently bonded on complementary hybridized nucleic acid strands, resulting in an efficient, specific, and permanent bond that may be used in many biological and nanotechnological applications.

Oligonucleotides

As used herein, the term "oligonucleotide" includes two or more nucleomonomers covalently coupled to each other by linkages or substitute linkages. An oligonucleotide may comprise, for example, between a few (e.g., 7, 10, 12, 15) or a few hundred (e.g., 100, 200, 300, or 400) nucleomonomers. For example, an oligonucleotide of the invention preferably comprises between about 10 and about 50 nucleomonomers, between about 15 and about 40, or between about 20 and about 30 nucleomonomers. In one embodiment, an oligonucleotide comprises about 25 nucleomonomers. In another embodiment, an oligonucleotide comprises greater than about 25 nucleomonomers. Oligonucleotides may comprise, for example, oligonucleotides, oligonucleosides, polydeoxyribonucleotides (containing 2'-deoxy-D-ribose) or modified forms thereof, e.g., DNA, polyribonucleotides (containing D-ribose or modified forms or analogs thereof), RNA, or any other type of polynucleotide which is an N-glycoside or C-glycoside of a purine or pyrimidine base, or modified purine or pyrimidine base. The term oligonucleotide includes compositions in which adjacent nucleomonomers are linked via phosphorothioate, amide or other linkages (e.g., Neilsen, P. E., et al. 1991. *Science*. 254:1497). Generally, the term "linkage" refers to any physical connection, preferably covalent coupling, between two or more nucleic acid components, e.g., catalyzed by an enzyme such as a ligase. The term "oligonucleotide" includes any structure that serves as a scaffold or support for the bases of the oligonucleotide, where the scaffold permits binding to the target nucleic acid molecule in a sequence-dependent manner.

As used herein, an "sticky end" is a relatively short single-stranded nucleotide sequence on the 5'- or 3'-hydroxyl end of a double-stranded oligonucleotide molecule used to control the arrangement of linear segments of DNA (also referred to as an "extension," "protruding end," or "overhang").

As used herein, the term "base" includes the known purine and pyrimidine heterocyclic bases, deazapurines, and analogs (including heterocycl substituted analogs, e.g., aminoethyoxy phenoxazine), derivatives (e.g., 1-alkenyl-, 1-alkynyl-, heteroaromatic-, and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl)cytosine and 4,4-ethanocytosine). Other examples of suitable bases include non-purinyl and non-pyrimidinyl bases such as 2-aminopyridine and triazines As used herein, the term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

Oligonucleotides of the invention can be synthesized by any methods known in the art, e.g., using enzymatic synthesis and chemical synthesis. The oligonucleotides can be synthesized in vitro (e.g., using enzymatic synthesis and chemical synthesis) or in vivo (using recombinant DNA technology well known in the art.

In a preferred embodiment, chemical synthesis is used. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. J. Chromatog. 1985. 326:263; LaPlanche et al. 1986. *Nuc. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. No. 5,013,830; U.S. Pat. No. 5,214,135; U.S. Pat. No. 5,525,719; Kawasaki et al. 1993. *J. Med. Chem.* 36:831; WO 92/03568; U.S. Pat. No. 5,276,019; U.S. Pat. No. 5,264,423.

The synthesis method selected can depend on the length of the desired oligonucleotide and such choice is within the skill of the ordinary artisan. For example, the phosphoramidite and phosphite triester methods produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence can be purchased commercially.

The oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

Cinnamate

As used herein, a "crosslinker" is a chemical compound having two or more polymerizable groups. In general, any crosslinking compound may be used, so long as the polymerizable groups on the crosslinker are capable of forming a crosslinked co-polymer between the enzymes and the at least one monomer unit under the conditions used to form the nanocomplex. Examples of crosslinkers include compounds having two vinyl, acryl, alkylacryl, or methacryl groups. Examples of specific crosslinkers having two acryl groups include N,N'-methylenebisacrylamide and glycerol dimethacrylate. In preferred embodiments of the present invention, the crosslinker is cinnamate or a derivative thereof.

The term "binding" or "binds" as used herein are meant to include interactions between molecules that may be detected using, for example, a hybridization assay. The terms are also meant to include "binding" interactions between molecules. Interactions may be, for example, protein-protein, antibody-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

Cinnamate may be synthesized by any known method, such as, for example, but not limited to, the method shown in FIG. 6, starting with a solution of methyl 4-hydroxy cinnamate (1.58 g, 8.85 mmoles), 2,5-di-O-(p-toluyl)-2-deoxy-D-ribofuranosyl chloride (2.0 g, 5.9 mmoles), and cesium carbonate (3.27 g, 10.0 mmol) in tetrahydrofuran. In FIG. 6, the solution is stirred at room temperature overnight. The solution is filtered and the filtrate concentrated under high vacuum. The crude solid is purified by column chromatography (98.5:1.5 DCM:MeOH) to give 1.97 g (63%) of 4-hydroxy cinnamate-1'-β-deoxyriboside-3',5'-di-(p-toluoyl)ester ("Compound 1") as a white solid. Compound 1 is stirred in 1.93 ml (10.7 mmol) of sodium methoxide (30% w/v in MeOH) at room temperature for two days. The mixture is neutralized with a 10% acetic acid solution followed by extraction three times with DCM. The combined organic layers are washed with water and brine, and dried over $Na_2SO_4$. The solution is concentrated under high vacuum and the crude solid is purified by column chromatography (gradient 0-5% MeOH; DCM) to give 1.05 g (99.5%) of 4-hydroxy cinnamate-1'-β-deoxyriboside ("Compound 2") as a white solid. To a solution of Compound 2 (610.0 mg, 2.07 mmoles) and N,N-diisopropylethylamine (0.54 ml, 3.11 mmoles) in pyridine (anh.) is added 4,4'-dimethoxytriphenylmethyl chloride (351.2 mg, 1.04 mmol) and stirred at room temperature. Ater an hour, additional 4,4'-dimethoxytriphenylmethyl chloride (351.2 mg, 1.04 mmol) is added to the mixture and stirred for one hour. The solution is concentrated under high vacuum yielding a pasty yellow precipitate which is dissolved in ethyl acetate and washed with water, $NaHCO_3$, brine, and dried over $Na_2SO_4$. The crude material is purified by chromatography (1:1 ethyl acetate:hexanes; 1% triethyamine) to give 990.0 mg (80%) of 5'-O-(4,4'-dimethoxytrityl)-4-hydroxy cinnamate-1'-β-deoxyriboside ("Compound 3") as a white solid. To a solution of Compound 3 (690.0 mg, 1.16 mmol), and N—N-diisopropylethylamine (0.41 ml, 2.32 mmol) in pyridine (anh.) is added 2-cyanoethyl N—N-diisopropyl chlorophosphoramidite (0.31 mL, 1.39 mmol) and stirred at room temperature for 30 minutes. The solution is concentrated under high vacuum and the precipitate is dissolved in ethyl acetate. The organic solution is washed with water, NaHCO3, brine, and dried over Na2SO4. The crude material purified by chromatography (1:1 ethyl acetate:hexanes; 1% triethylamine) to give 761.7 mg (82%) of 5'-O-(4,4'-dimethoxytrityl)-4-hydroxy cinnamate-1'-β-deoxyriboside-3'-O-(cyanoethoxy-N,N-diisopropylamino) phosphoramidite ("Compound 4").

Biochip/Array

Nucleic acids used in the present invention can be immobilized to or applied to an array or "biochip". As used herein, a "biochip" refers to a solid substrate having a generally planar surface to which a capture reagent (adsorbent) is attached. Frequently, the surface of the biochip comprises a plurality of addressable locations, each of which location has the capture reagent bound there. Biochips can be adapted to engage a probe interface and, therefore, function as probes. In practicing the methods of the invention, any known array and/or method of making and using arrays can be incorporated in whole or in part, or variations thereof, as disclosed, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston, *Curr. Biol.* 8:R171-R174, 1998; Schummer, *Biotechniques* 23:1087-1092, 1997; Kern, *Biotechniques* 23:120-124, 1997; Solinas-Toldo, *Genes, Chromosomes & Cancer* 20:399-407, 1997; Bowtell, *Nature Genetics Supp.* 21:25-32, 1999. See also published U.S. Patent Applications Nos. 20010018642; 20010019827; 20010016322; 20010014449; 20010014448; 20010012537; 20010008765.

As used herein, a "substrate" refers to the material to which the surface nucleic acides of the presently claimed compositions and methods are attached. The substrate may be any material, such as a membrane, glass, plastic, bead, nanoparticle, or photonic/plasmodic structure, and may be solid, semi-solid, fibrous, capillary or porous.

Arrays are generically a plurality of "target elements" or "spots," each target element containing a defined amount of one or more biologically molecules, e.g., polypeptides, nucleic acid molecules, or probes, immobilized at discrete locations on a substrate surface. In preferred embodiments, the plurality of spots comprises nucleic acid segments, immobilized at preferably at least about 50, at least about 100, at least about 300, or at least about 500 discrete locations on the surface. The plurality may comprise multiple repeats of the same nucleic acid segments to produce, e.g., duplicate spots, triplicate spots, quadruplicate spots, quintuplicate spots, etc.

As used herein, the term "target gene" includes polynucleotides comprising a region that encodes a polypeptide or polynucleotide region that regulates replication, transcription, translation, or other process important in expression of the target protein or a polynucleotide comprising a region that encodes the target polypeptide and a region that regulates expression of the target polypeptide. The "target gene" to which an RNA molecule of the invention is directed may be associated with a pathological condition. For example, the gene may be a pathogen-associated gene, e.g., a viral gene, a tumor-associated gene, or an autoimmune disease-associated gene. The target gene may also be a heterologous gene expressed in a recombinant cell or a genetically altered organism. By determining or modulating (e.g., inhibiting) the function of such a gene, valuable information and therapeutic benefits in medicine, veterinary medicine, and biology may be obtained.

A "biologically active agent" or an active agent of this invention intends one or more of an isolated or recombinant polypeptide, an isolated or recombinant polynucleotide, a vector, an isolated host cell, or an antibody, as well as compositions comprising one or more of same.

As used herein "analyte" refers to any component of a sample that is desired to be detected. The term can refer to a single component or a plurality of components in the sample.

In an embodiment of the present invention, the immobilized nucleic acid molecules are contacted with a linker strand comprising cinnamate for specific binding, e.g., hybridization. As used herein, "hybridization" involves free, single-stranded stretches of nucleic acids. Accordingly, a nucleic-acid network may be regulated by the availability of these free strands. "Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of "stringent" hybridization conditions include, but are not limited to: incubation temperatures of about 25° C. to about 37° C.; hybridization buffer concentrations of about 6× standard sodium citrate (SSC) to about 10×SSC; formamide concentrations of about 0% to about 25%; and wash solutions of about 6×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

Once UV light is applied to any portion of the array desired, covalently binding the linker strand to the nucleic acid segment immobilized on the biochip, the linker strand may further hybridize to a target element. Target elements may contain, but are not limited to, whole or partial DNA sequences, reference sequences, such as positive and negative controls, and the like. The target elements of the arrays may be arranged on the substrate surface at different sizes and different densities. Different target elements of the arrays can have the same molecular species, but, at different amounts, densities, sizes, labeled or unlabeled, and the like. The target element sizes and densities will depend upon a number of factors, such as the nature of the label (the immobilized molecule can also be labeled), the substrate support (it is solid, semi-solid, fibrous, capillary or porous), and the like.

Each target element may comprise substantially the same nucleic acid sequences, or, a mixture of nucleic acids of different lengths and/or sequences. Thus, for example, a target element may contain more than one copy of a cloned piece of DNA, and each copy may be broken into fragments of different lengths, as described herein. The length and complexity of the nucleic acid fixed onto the biochip surface is not critical to the invention. The biochip can comprise nucleic acids immobilized on any substrate, e.g., a solid surface (e.g., nitrocellulose, glass, quartz, fused silica, plastics and the like). See, e.g., U.S. Pat. No. 6,063,338 describing multi-well platforms containing cycloolefin polymers if fluorescence is to be measured. Arrays used in the methods of the invention can comprise housing containing components for controlling humidity and temperature during the hybridization and wash reactions.

Many methods for immobilizing nucleic acids on a variety of solid surfaces are known in the art. For instance, the solid surface may be a membrane, glass, plastic, or a bead. The desired component may be covalently bound or noncovalently attached through nonspecific binding. The immobilization of nucleic acids on solid surfaces is discussed more fully below.

A wide variety of organic and inorganic polymers, as well as other materials, both natural and synthetic, may be employed as the material for the solid surface. Illustrative solid surfaces include nitrocellulose, nylon, glass, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition substances that form gels can be used. Such materials include proteins (e.g., gelatins), lipopolysaccharides, silicates, agarose and polyacrylamides. Where the solid surface is porous, various pore sizes may be employed depending upon the nature of the system.

In preparing the surface of a solid support for array printing, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like.

If covalent bonding between a compound and the surface is desired, the surface may be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. For example, methods for immobilizing nucleic acids by introduction of various functional groups to the molecules is known (see, e.g., Bischoff et al., *Anal. Biochem.* 164:336-344, 1987); Kremsky et al., *Nucl. Acids Res.* 15:2891-2910, 1987). Modified nucleotides can be placed on the target using PCR primers containing the modified nucleotide, or by enzymatic end labeling with modified nucleotides.

Alternative surfaces include derivatized surfaces such as chemically coated glass slides. On example, is the CodeLink™ Activated Slide from Amersham Biosciences. These slides are coated with a novel 3-D surface chemistry comprised of a long-chain, hydrophilic polymer containing amine-reactive groups, to react with and covalently immobilize amine-modified DNA for microarrays. This polymer is covalently crosslinked to itself and to the surface of the slide and is designed to orient the immobilized DNA away from the surface of the slide to improve hybridization. Another such 3D slide is UltraGap™, sold by Dow Corning.

Use of membrane supports (e.g., nitrocellulose, nylon, polypropylene) for the nucleic acid arrays of the invention is advantageous because of well developed technology employing manual and robotic methods of arraying targets at relatively high element densities (e.g., up to 30-40/cm$^2$). In addition, such membranes are generally available and protocols and equipment for hybridization to membranes is well known. Many membrane materials, however, have considerable fluorescence emission, where fluorescent labels are used to detect hybridization.

Aside from the demonstrated applications with colloids and on substrates, the specific and efficient crosslinking of the cinnamate crosslinker may also be used in other applications to make assembled structures. For example, DNA directed nano-particle assembly, emulsion droplets, and plasmonic materials are also contemplated as substrates.

To optimize a given assay format one of skill can determine sensitivity of fluorescence detection for different combinations of membrane type, fluorophore, excitation and emission bands, spot size and the like. In addition, low fluorescence background membranes have been described (see, e.g., Chu et al., *Electrophoresis* 13:105-114, 1992).

The sensitivity for detection of spots of various diameters on the candidate membranes can be readily determined by, for example, spotting a dilution series of fluorescently end labeled DNA fragments. These spots are then imaged using conventional fluorescence microscopy. The sensitivity, linearity, and dynamic range achievable from the various combinations of fluorophore and membranes can thus be determined. Serial dilutions of pairs of fluorophore in known relative proportions can also be analyzed to determine the accuracy with which fluorescence ratio measurements reflect actual fluorophore ratios over the dynamic range permitted by the detectors and membrane fluorescence.

Arrays on substrates with much lower fluorescence than membranes, such as glass, quartz, or small beads, can achieve much better sensitivity. For example, elements of various sizes, ranging from about 1 mm diameter down to about 1 μm can be used with these materials. Small array members containing small amounts of concentrated target DNA are conveniently used for high complexity comparative hybridizations since the total amount of probe available for binding to each element will be limited. Thus, it is advantageous to have small array members that contain a small amount of concentrated target DNA so that the signal that is obtained is highly localized and bright. Such small array members are typically used in arrays with densities greater than 10$^4$/cm$^2$. Relatively simple approaches capable of quantitative fluorescent imaging of 1 cm$^2$ areas have been described that permit acquisition of data from a large number of members in a single image (see, e.g., Wittrup et al., *Cytometry* 16:206-213, Hybridization to nucleic acids attached to beads is accomplished by suspending them in the hybridization mix, and then depositing them on the glass substrate for analysis after washing with eluent. As used herein, "eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature. Alternatively, paramagnetic particles, such as ferric oxide particles, with or without avidin coating, can be used.

The invention will now be described in greater detail by reference to the following non-limiting examples.

EXAMPLES

Example 1

Specificity and Efficiency of Cinnamate Binding in Solution

For the purposes of the experiments described herein, cinnamate-functionalized phosphoramidite was obtained in four high yielding steps. The glycosylation of the cinnamate derivative with Hoffer's α-chloro saccharide was achieved using cesium carbonate. Sodium methoxide was employed in order to remove the p-tol protecting groups, which afforded free hydroxyl groups at the 3' and 5' positions of the saccharide. Finally, the 5'-OH was protected with dimethoxytritylchloride followed by conversion of the 3'-OH to a phosphoramidite. The cinnamate-containing phosphoramidite was incorporated into a DNA oligonucleotide using conventional procedures.

All UV exposure took place as follows: UV power output was measured with a SiC photodiode with peak sensitivity at 340 nm. The power output 1 cm from the UV lamp was ~0.6 mW/cm$^2$ or ~10 photons/sec-nm2. For internal Hg lamp with ×100 Leica air objective on Leica DMRXA microscope with Leica Type A filter cube, power output is ~60 photons/sec-nm$^2$ as in the crosslinking experiment on particles. For the external Hg lamp with ×63 Leica air objective, power output is ~30 mW/cm$^2$ or ~500 photons/sec-nm$^2$ as used in Example 3 below.

To determine whether DNA strands in solution bind only selectively with UV exposure, a denaturing gel, FIG. 2(A) is used to dehybridize the DNA strands without disruption of the covalently bound strands. The gels contained 8.3 M urea and were run at 55° C. The running buffer consisted of 89 mM Tris, HCl, pH 8.0, 89 mM Boric acid, 2 mM EDTA (TBE). The sample buffer consisted of 10 mM NaOH, 1 mM EDTA, a trace amount of Xylene Cyanol FF and Bromophenol Blue tracking dye. Gels were run on a Hoefer SE 600 electrophoresis unit (31 V·cm, constant voltage). When further denaturation was required, a 6% acrylamide gel solution containing 7.0 M urea and 41% formamide, or a 4% acrylamide gel solution containing 6.8 M urea and 47% formamide were substituted for a regular denaturing gel. The constructs used had complementary cinnamate-modified sticky ends and the same double strand formed on hybridization, wherein the hybridized constructs lacked sticky ends. The constructs are referred to as "C" and "D" and the hybridized version as "CD," wherein C has the sequence 5'-ATCGCTACCCTTCG-CACAGTCAATCCAGAGAGCCCTGC-CTTTCATTACGACCAAGT-crosslinker-TATGA-3' (SEQ ID NO:1), D has the sequence 5'-ATCGCTACCCTTCGCA-CAGTCAATCCAGAGAGCCCTGC-CTTTCATTACGATCATA-crosslinker-ACTTGG-3' (SEQ ID NO:2), and CS has the sequence 5'-TCGTAATGAAAG-GCAGGGCTCTCTGGATTGACTGTGC-GAAGGGTAGCGAT-3' (SEQ ID NO:3). The cinnamate nucleoside was inserted at the 7$^{th}$ nucleoside position (in the 5' to 3' direction), within the 11-base sticky end of the C strand as well as the associated 6$^{th}$ base position on the D strand. In all experiments shown in FIG. 2A, the DNA strands were annealed with an equal number of CS strands to hybridize and form a construct with a 50 nucleotide pair rigid duplex followed by an 11 nucleoside sticky end. Lanes 1, 4, and 7 contain strands C and CS only. Lanes 2, 5, and 8 contain D and CS only. Neither temperature nor UV exposure prompt the hybridization of the cinnamate-containing strands C with C or D with D. Lanes 3, 6, and 9 contain both strands C and D, and CS. Even though C and D hybridize, without UV exposure there is no crosslinking, as seen in lane 3. However, after a five-minute exposure to UV light (10 Photons/sec-nm2), there is substantial crosslinking in lane 6, which is even stronger after 15 minute UV light exposure, as shown in lane 9. Thus, two DNA strands are only covalently bonded when the two cinnamate nucleosides are held in juxtaposition by flanking complementary sequences in the sticky ends.

Figure 7:
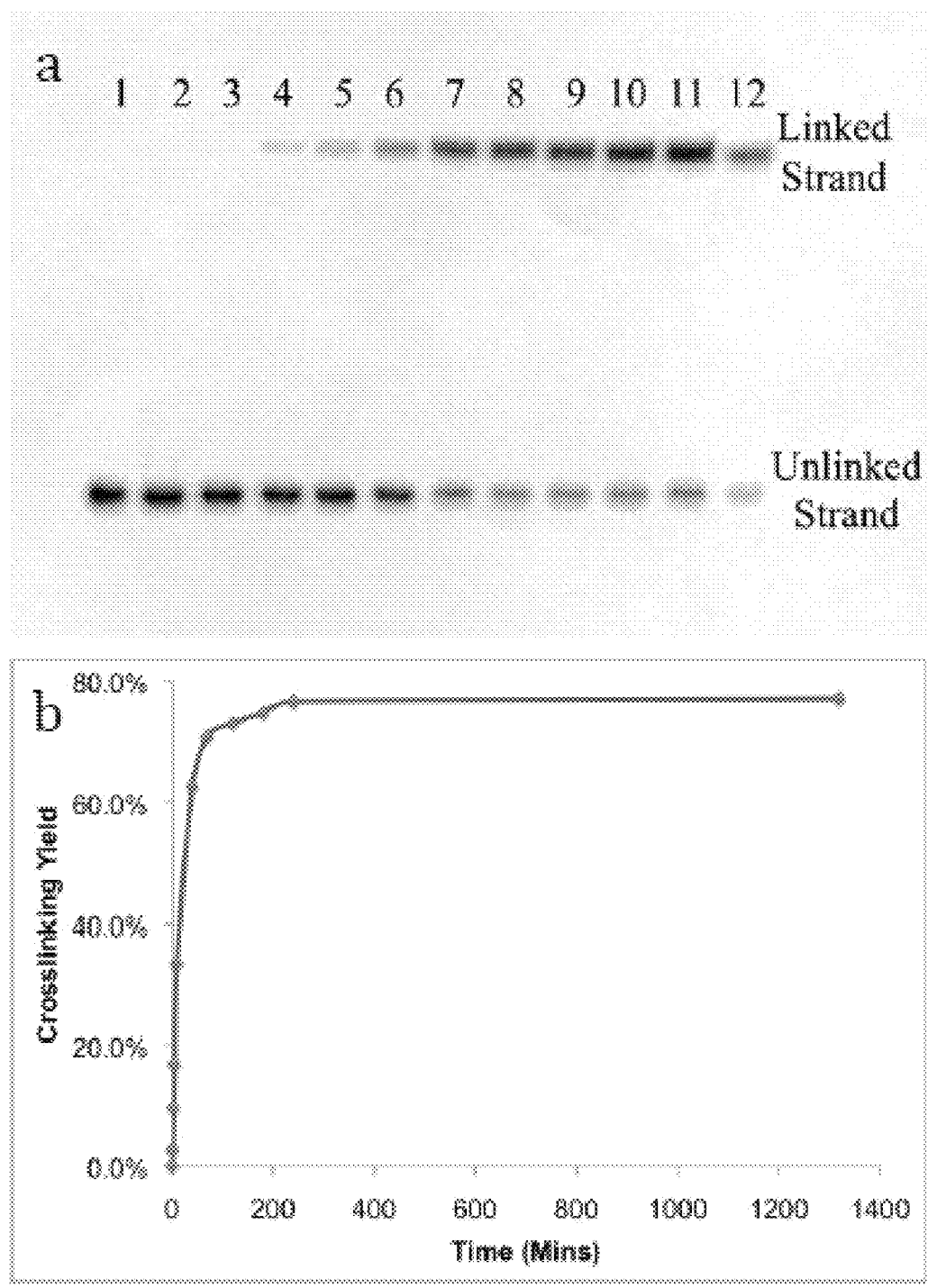
FIG. 7A is an audioradiogram of a 10% denaturing gel run wherein one strand of duplex was labeled radioactively by $^{32}P$. Lane 1 is the control, with lanes 2-12 showing progressive exposure to 360 nm UV light for 0, 1, 3, 5, 10, 40, 70, 120, 180, 240, and 1320 minutes respectively. 7B is a histogram showing the crosslinking yield.
Figure 8:
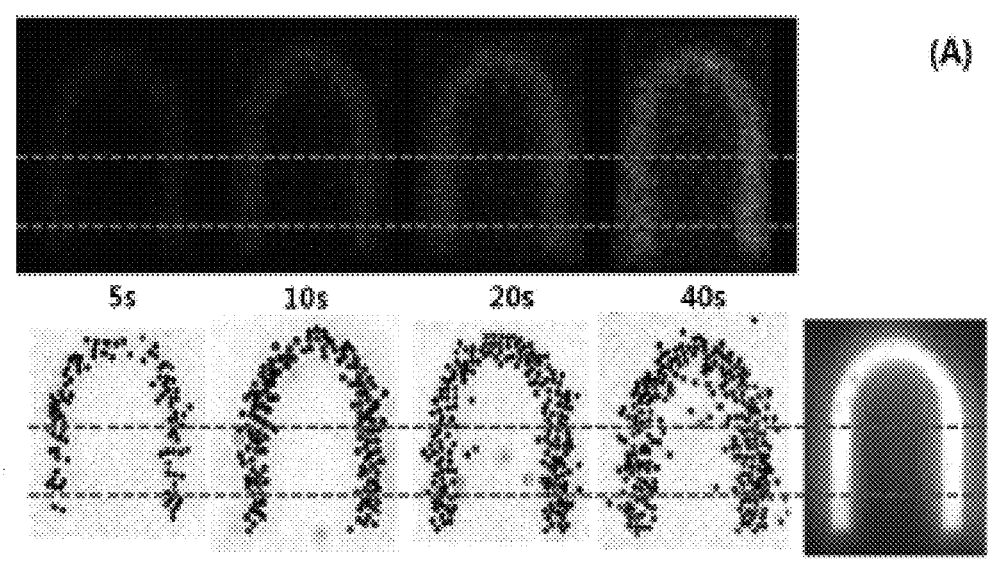
FIG. 8 is a series of photographs showing reversible aggregation-dissociation behavior or DNA coated colloids after UV exposure for 2 s, 5 s, 10 s, or 15 s), the behavior of particles after heating. Both 10 s and 15 s achieve ~100% particle cross-linking efficiency.
Figure 9:
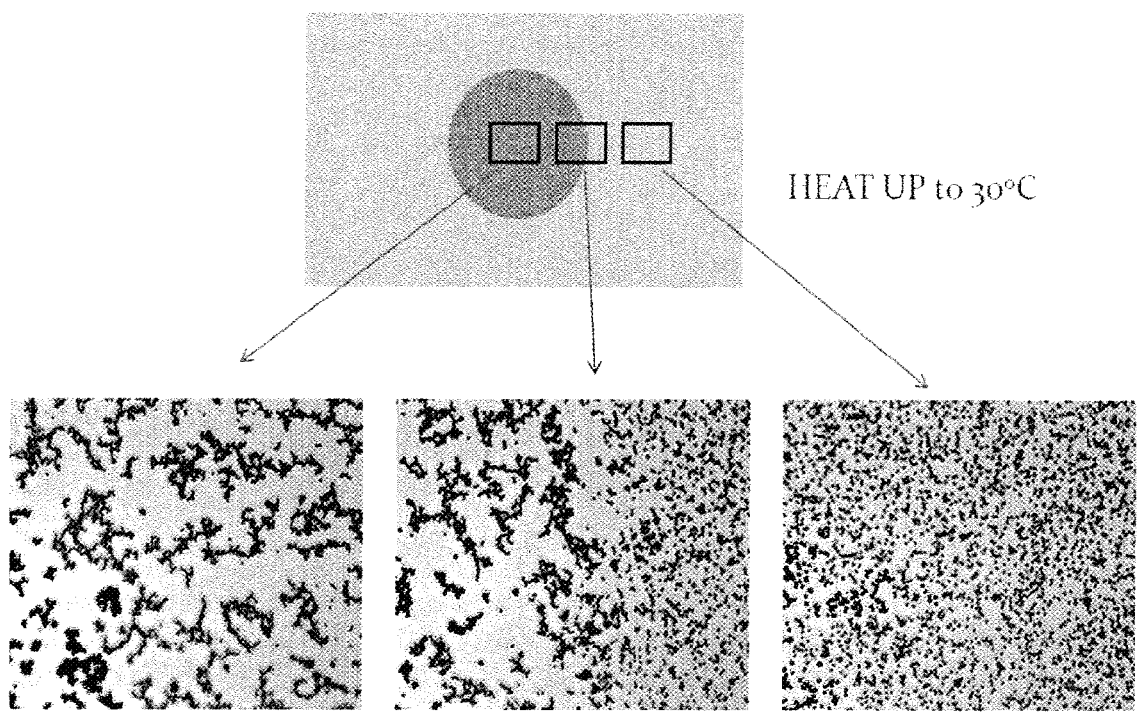
FIG. 9 is a set of photographs showing an approximately 1 mm circular region of UV exposure (defined by the projection of circular aperture on the microscope), after UV exposure and cross-link at 20 degrees Celsius. Inside the exposure region, as shown at left, crosslinking leads to irreversible clusters. Outside the exposure region, as shown at right, temperature reversible behavior remains. The phenomenon is most evident at the boundary, shown in the middle photograph.

The efficiency and exposure time dependence of cinnamate crosslinking was tested by preparing two 40-mer DNA strands with complementary sequences with the cinnamate groups incorporated in each strand in place of a complementary pair. The cinnamate groups are held in close proximity, <1 nm, by the DNA hybridization of the flanking base pairs. The specific sequences used are 5'-GCTACCCTTCGCA-CAGTCAA-crosslinker-TCCAGAGAGCCCTGCCTTTC-3' (SEQ ID NO:4) and 5'-GAAAGGCAGGGCTCTCTGGA-crosslinker-TTGACTGTGCGAAGGGTAGC-3' (SEQ ID NO:5). The denaturing gel (FIG. 7) was run at 55° C. The first lane is a sample with only A strands. In lanes 2-12, the complementary sequences have been hybridized by annealing them from 90° C. to 4° C. over a period of 2 hours. At 4° C., they have been exposed to UV for various lengths of time to form the permanent cyclobutyl crosslink between the strands via the 2+2 cycloaddition between two cinnamate groups. A denaturing gel indicates no hybridized bonds, thus indicating the formation of larger molecules via a covalent link. Hence, the lower bands with the same mobility as seen in the first lane consist of uncrosslinked single strands of SEQ ID NO:4 or 5. The upper bands with lower mobility correspond to the higher molecular weight of crosslinked SEQ ID NO:4-SEQ ID NO:5 strands.

FIG. 7B shows a plot of the crosslinking yield, the intensity of the upper band in FIG. 7A divided by the sum of the intensities of the upper and lower bands versus the UV exposure time. The UV source used in this experiment was a UV lamp whose power output was measured with a SiC photodiode with peak sensitivity at 340 nm. Power output 1 cm from the lamp was approximately 0.6 mW/cm$^2$ or approximately 10 photons/sec-nm$^2$. An exposure time of one hour is sufficient to establish most of the cinnamate crosslinks that will form, an effective linking cross section of $3\times10^{-5}$ nm$^2$.

Example 2

Cinnamate-Containing DNA Allows for the Permanent and Specific Binding of Colloidal Particles In order to investigate the permanent joining of colloidal particles with UV light exposure of cinnamate-containing DNA, biotin (and 4 bases PEG) were added to sequences C and D as the terminating group at the 5' end, in order to bind to streptavidin coated particles. A similar construct was made where the sticky ends were self-complementary palindromic sequences (P) lacking cinnamate. To show that a colloid may be functionalized with different DNA strands, five sets of particles were created with different coatings using C, D, P, C+P, and D+P. The C+P (D+P) particles have half of their surface randomly coated with P strands and half with C (D) strands. The attached DNA sequence was designed such that the P-coated particles had a lower melting temperature (about 40° C.) than the C and D complementary pair (about 45° C.). Four sets of experiments were performed using the following protocol:

Each sample was annealed by cooling it over a one hour period from 55° C. to room temperature. Each sample was then exposed to UV (16 seconds at 60 photons/sec-nm2) at room temperature and heated to 55° C. for ten minutes. The first set with P-coated particles dissociated completely upon heating, indicating that UV exposure did not link these DNA functionalized particles. The second set with a mixture of particles C and D and the third set with a mixture of particles C+P and D+P showed little dissociation. UV irradiation successfully crosslinked the cinnamate modified paired strands and the palindrome did not interfere with the cinnamate crosslinking, as shown in FIG. 2B. The set with only particles C+P, however, (FIG. 2B, right), almost dissociated completely after heating. Though the cinnamate groups on the non-complementary strands of two particles were held together within a range of about 20 nm, UV exposure was not effective for crosslinking in this case.

FIG. 2C compares the fraction of unbound particles for the equal mixture of complementary cinnamate-modified C and D particles to the C+P particles. This is a particularly sensitive measure since these particles are typically joined by about 150 bonds. If any pair is crosslinked, the particles remain stuck together. This data demonstrates that the selectivity is at least 300:1.

Multifunctional surfaces may also be created using the present methods. For example, as shown in FIG. 3, a three-component structure was designed consisting of a surface strand (SS), with a sequence of 5'-RSS-50basesBackbone-TTGAGAAATGC-cinnamate-CGTAAAGAGTT-3' (SEQ ID NO:6); a particle strand (PS), with a sequence of 5'-GGAT-GAAGATG-50basesBackbone-BiotinTEG-3' (SEQ ID NO:7); and a linker strand (LS), having a sequence of 5'-CATCTTCATCCAACTCTTTACG-cinnamate-GCATTTCTCAA-3' (SEQ ID NO:8). The SS is attached to a gilded surface by a disulfide group, followed by a 50-bp backbone (as shown in FIG. 3A), and an active 22-bp sticky end with cinnamate. The linker strand has two parts: a cinnamate containing sequence complementary to the SS, and a functional sequence that is designed to bind specifically to the particles or other materials in the system. Finally, the target material, here the particles, have a complement to the functional strand. The LS-SS DNA melting temperature without UV radiation is approximately 45° C., which ensures highly efficient crosslinking at room temperature.

A Leica DMRXA microscope with Qimaging Retiga 1300 camera and Leica external Hg lamp was used to observe colloidal results. Leica Type A filter cube was used to provide 365 nm wavelength UV light for the cinnamate crosslinking Black field masks were purchased from FineLine imaging and placed at the aperture conjugated to the sample image.

Example 3

Use of Cinnamate-Containing DNA in Functional Photolithoraphy

In order to confirm the applicability of cinnamate-containing DNA in functional photolithography methods, a surface was first functionalized as shown in FIG. 3B. A cover slip (2.5 cm by 2.5 cm) was first cleaned using acetone, plasma etched by SPI supplies Plasma Prep II, and then evaporated with 5 nm chromium and 40 nm thickness gold (SIGMA-ALDRICH 99.999%) using a BAL-TEC MCS 010 Multi Control System. A thiol attached surface strand (72 bp) was first hybridized with its 49 bp complementary strand (SEQ ID NO:9; 5'-CGT AAT GAA AGG CAG GGC TCT CTG GAT TGA CTG TGC GAA GGG TAG CGA T-3') from 95° C. to 25° C. to form a rigid double stranded backbone and then incubated on the gold surface for 12 hours under the following conditions: 25° C. normal buffer (10 mM PB, 50 mM NaCl, 1% w/w F127) and thiol DNA concentration 40 μM. The small incubation chamber was sealed to avoid evaporation. After incubation, extra strands were washed out using a 55° C. normal buffer repeated three times. This resulted in ~3000 μm$^{-2}$ DNA density as determined by radioactive measurement. The linker strands were then hybridized to the surface strands by annealing them from 55° C. to 25° C. for 30 minutes (steps 1 and 2). The samples were then exposed to UV light to permanently cross-link the surface and linker strands in the exposed areas (step 3). Finally, the sample was heated to 55° C. and washed three times to de-hybridize the unlinked strands (step 4). The functionalized surface was then capable of reversibly binding colloids to the patterned regions. To make spatially dependent DNA multifunctionalized surfaces, it is necessary to repeat steps 3 and 4 at different places with different linker strands.

In order to provide the in situ temperature control described above, 1000Ω ITO glass was placed on a 3 mm thick copper plate, two ends of which were connected to peltiers (2.5 cm by 2.5 cm), then to a thermal sink with constant temperature. With LakeShore DRC 93C Temperature Controller and LakeShore PT-111 temperature sensor, the temperature is controllable with <0.5° C. relative error.

The colloids used were created as follows: 1 μm streptavidin covered polystyrene particles were purchased from Invitrogen (Dynabeads MyOne Streptavidin C1). Biotinylated particle strands with a double stranded backbone were incubated with particles for one hour under the following conditions: 25° C., light shaking, normal buffer, particle volume fraction 0.05%, and biotinylated strand concentration of 0.5 μM. Particles were washed by centrifuging and re-suspension three times to wash out extra strands. This resulted ~6400 μm$^{-2}$ DNA density as determined by radioactive measurement.

FIG. 4 shows results for the photolithography using the above procedure and a NYU mask. A Leica DMRXA microscope with Qimaging Retiga 1300 camera and Leica external Hg lamp was used to observe colloidal results. A Leica DM6000 CS confocal microscope was used to take all fluorescent images. An argon laser was used for excitation. Streptavidin with Alexa Fluror 488 (Invitrogen) was used to dye the biotinylated complementary DNA particle strand, which was conjugated to the DNA sticky end in the lithography pattern. A high salt concentration buffer (500 nM NaCl) was used to stabilize the interaction. The particles had a gravitational height, $k_B T/mg$ ~1 micron, and hence sediment. Therefore, samples were turned upside down after particle binding to show clearly which particles were attached. FIG. 4A depicts an image of the exposed Y along with a decoration by 1 micron PS coated polystyrene spheres as well as by PS attached to fluorescein labeled streptavidin. Both fluorescent and colloid pictures show a minimum feature size of ~2 μm (FIGS. 4B and C). The binding between the linker strand and either the colloids or the labeled DNA strands is thermoreversible. Upon heating, the colloids sediment away from the letters and the PS DNA strands diffuse away. Cooling leads to reassociation. It was also confirmed that the effective cross section of cinnamate by colloid-surface melting temperatures is $3 \times 10^{-5}$ nm$^2$.

To make a spatially dependent multi-functionalized surface and demonstrate the versatility of implementations of the described methods, the photolithography as described above (steps 1 to 6), and then repeated steps 3 and 4 on a different region of the gold surface using modified linker strands (steps 7 and 8). The new linker strand 2 (LS2) contains a functional molecule (biotin in this case) at its 5' end, unlike the single-stranded sticky-end of LS. The newly functionalized region of the gold surface with LS2 strands was visualized by the conjugation of red fluorescent streptavidin. The sticky LS in the first exposure region remained functional as tested by the addition of fluorescently labelled PS strands (step 9).

FIG. 4c shows the result of a multi-functionalization experiment, after step 9 of FIG. 3b. The green fluorescently labelled PS strand sticks to the LS patterned region (letters of 'materials' in FIG. 4c, left) by complementary DNA hybridization. Red streptavidin binds to the LS2-patterned biotin region (letters of 'nature' in FIG. 4c, left). The distinct colors in separate filtering channels confirmed the successful patterning of two different functions without interference.

Pattern resolution was investigated in FIG. 5A, in which an inverted "U" shape was exposed to UV for different times, decorated with fluorescently labeled DNA and with colloids. Light intensity and particle concentration were analyzed for a cut through the two straight legs of the inverted "U". The dark black curves represent relative particle concentration. The last panel is the exposure profile. The light jagged shaped curves give the intensity of green fluorescent light from confocal images, and the corresponding smooth curves are a linear rescaling of the exposed peaks based on estimated coverage (from left to right: 8%, 15%, 28%, and 48%). The images and curves show that short exposure times (5 s) led to weak fluorescent light, and non-uniformity in colloidal pattern (FIG. 5A, left) due to inhomogenous crosslinking Increasing exposure time yielded a stronger fluorescent signal and complete colloidal patterning, but also lowered the pattern resolution by producing undesired crosslinking in peripheral regions (FIG. 5A, right). Given that the lithographic system was quite basic, ~10 s exposure time was found to give a good balance between uniform functionalization and high resolution.

FIG. 5B shows the best resolution achieved by superimposing the pattern image on the colloid and fluorescent images, respectively. The line width is ~1.5 μm in the exposure pattern and ~2 μm in the fluorescent image, which suggests at least 1 μm resolution on the edge. This resolution is slightly lower than standard UV photolithography in vacuum (~0.8 μm) or direct laser writing due to the presence of buffer. However, the results are within the parameters for use in DNA chips for gene identification or colloidal self-assembly.

Example 4

Use of Cinnamate Crosslinking in Assembly

To demonstrate the use of the present compositions and methods in assembly of structures, a pair of cinnamate nucleosides is inserted into the middle of two short Watson-Crick complementary sequencs which are then positioned as surface nucleic acides on a substrate selected from the group consisting of nanoparticles, emulsion droplets, and photonic or plasmodic particles. The covalent crosslinking is activated by UV exposure. It is then possible to selectively and permanently link the assembled constructs, including nano-particle crystals, aggregates from emulsion droplets, and photonic/plasmonic structures. Once the assembled construct is covalently linked, the bonds are uninfluenced by factors like temperature and buffer condition. Cinnamate crosslinking of plasmonic structures in stability in dehydrated condition, a useful feature in fabricating solid state devices.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A composition comprising:
   a first substrate having a first surface nucleic acid strand comprising a first cinnamate functional group and forming a first sticky end,
   a second substrate having a second surface nucleic acid strand comprising a second cinnamate functional group and forming a second sticky end, the first sticky end and the second sticky end substantially complementary and hybridizable with each other;
   wherein the first substrate and the second substrate are covalently bonded via the first cinnamate functional group and the second cinnamate functional group.

2. The composition of claim 1, wherein the substrate is selected from the group consisting of a membrane, glass, plastic, bead, emulsion droplet, nanoparticle, or photonic/plasmonic structure, and is solid, semi-solid, fibrous, capillary or porous.

3. The composition of claim 1, wherein the covalent bonding is the result of a hybridization step and a subsequent UV exposure step.

4. The composition of claim 3, wherein the hybridization step takes place as a result of a heating step.

5. The composition of claim 1, wherein the 5' end of the nucleic acid strand is connected to a tetraethylene glycol spacer terminated by a biotin group.

6. The composition of claim 1, wherein the sticky end has a sequence of 5'-TACG-linker-CGTA-3' and the linker is cinnamate.

7. The composition of claim 3, wherein the UV exposure takes place for less than 30 minutes.

8. The composition of claim 3, wherein the UV exposure takes place for less than 15 seconds at an intensity of about 3.6 mW/cm$^3$.

* * * * *

SEQUENCE LISTING

```
<160> NUMBER OF SEQ ID NOS: 9

<210> SEQ ID NO 1
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (56)..(57)
<223> OTHER INFORMATION: Nucleotides at these positions are separated
      by crosslinker
<220> FEATURE:
<223> OTHER INFORMATION: See specification as filed for detailed
      description of substitutions and preferred embodiments

<400> SEQUENCE: 1
atcgctaccc ttcgcacagt caatccagag agccctgcct ttcattacga ccaagttatg      60
a                                                                     61

<210> SEQ ID NO 2
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (55)..(56)
<223> OTHER INFORMATION: Nucleotides at these positions are separated by
      crosslinker
<220> FEATURE:
<223> OTHER INFORMATION: See specification as filed for detailed
      description of substitutions and preferred embodiments

<400> SEQUENCE: 2
atcgctaccc ttcgcacagt caatccagag agccctgcct ttcattacga tcataacttg      60
g                                                                     61

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtaatgaa aggcagggct ctctggattg actgtgcgaa gggtagcgat               50

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)..(21)
<223> OTHER INFORMATION: Nucleotides at these positions are separated by
```

```
        crosslinker
<220> FEATURE:
<223> OTHER INFORMATION: See specification as filed for detailed
      description of substitutions and preferred embodiments

<400> SEQUENCE: 4
gctacccttc gcacagtcaa tccagagagc cctgcctttc                          40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)..(21)
<223> OTHER INFORMATION: Nucleotides at these positions are separated by
      crosslinker
<220> FEATURE:
<223> OTHER INFORMATION: See specification as filed for detailed
      description of substitutions and preferred embodiments

<400> SEQUENCE: 5
gaaaggcagg gctctctgga ttgactgtgc gaagggtagc                          40

<210> SEQ ID NO 6
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(50)
<223> OTHER INFORMATION: a, c, t, g, unknown or other
<220> FEATURE:
<221> NAME/KEY: misc_feature
<222> LOCATION: (61)..(62)
<223> OTHER INFORMATION: Nucleotides at these positions are separated by
      cinnamate crosslinker
<220> FEATURE:
<223> OTHER INFORMATION: See specification as filed for detailed
      description of substitutions and preferred embodiments

<400> SEQUENCE: 6
nnnnnnnnnn nnnnnnnnnn nnnnnnnnnn nnnnnnnnnn nnnnnnnnnn ttgagaaatg    60
ccgtaaagag tt                                                        72

<210> SEQ ID NO 7
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(61)
<223> OTHER INFORMATION: a, c, t, g, unknown or other
<220> FEATURE:
<223> OTHER INFORMATION: 3'-BiotinTEG

<400> SEQUENCE: 7
ggatgaagat gnnnnnnnnn nnnnnnnnnn nnnnnnnnnn nnnnnnnnnn nnnnnnnnn     60 n                                                                    61
```

```
<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (22)..(23)
<223> OTHER INFORMATION: Nucleotides at these positions are separated by
      cinnamate crosslinker
<220> FEATURE:
<223> OTHER INFORMATION: See specification as filed for detailed
      description of substitutions and preferred embodiments

<400> SEQUENCE: 8
catcttcatc caactcttta cggcatttct caa                                    33

<210> SEQ ID NO 9
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgtaatgaaa ggcagggctc tctggattga ctgtgcgaag ggtagcgat                   49
```